United States Patent [19]
Valente et al.

[11] Patent Number: 6,025,534
[45] Date of Patent: Feb. 15, 2000

[54] OLEFIN POLYMERIZATION PROCESS

[75] Inventors: Anthony M. Valente, Yorktown; David B. Johnson, Hayes, both of Va.; George A. Huff, Jr., Naperville; Robert L. Mehlberg, Wheaton, both of Ill.

[73] Assignee: BP Amoco Corporation, Chicago, Ill.

[21] Appl. No.: 09/056,212

[22] Filed: Apr. 7, 1998

[51] Int. Cl.[7] .................................................... C07C 2/02
[52] U.S. Cl. ..................... 585/529; 585/502; 585/520; 585/527
[58] Field of Search .................... 585/502, 514, 585/529, 527, 520; 502/31; 526/233, 290

[56] References Cited

U.S. PATENT DOCUMENTS

| | | | |
|---|---|---|---|
| 2,120,702 | 6/1938 | Ipatieff et al. | 23/233 |
| 2,658,933 | 11/1953 | May et al. | 260/683.15 |
| 3,050,472 | 8/1962 | Morrell | 252/435 |
| 3,050,473 | 8/1962 | Morrell | 252/435 |
| 3,132,109 | 5/1964 | Morrell | 252/435 |
| 4,028,430 | 6/1977 | Stine et al. | 260/683.43 |
| 4,062,801 | 12/1977 | Burton et al. | 252/414 |
| 4,857,666 | 8/1989 | Barger et al. | 585/323 |
| 5,648,579 | 7/1997 | Kulprathipanja et al. | 585/447 |
| 5,932,778 | 8/1999 | Valente et al. | 585/529 |

FOREIGN PATENT DOCUMENTS

| | | | |
|---|---|---|---|
| 1055921 | 6/1979 | Canada | B01J 27/14 |
| 518163 | 2/1940 | United Kingdom | 585/529 |
| 863539 | 3/1961 | United Kingdom . | |

*Primary Examiner*—Fred Teskin
*Attorney, Agent, or Firm*—Richard A. Kretchmer; Frank J. Sroka

[57] ABSTRACT

A method is provided for regenerating a fixed bed of olefin polymerization catalyst which can be performed without taking the catalyst bed out of service. The method involves the use of two different olefin-containing feedstocks, wherein the first feedstock is a conventional olefin-containing feedstock which contains little if any content of aromatic compounds. The second feedstock contains a significant concentration of aromatic compounds. In the practice of the invention, the second feedstock is substituted for the first feedstock whenever catalyst regeneration is deemed appropriate, and the flow of the second feedstock to the catalyst bed is continued for a period of time which is effective to at least partially regenerate the catalyst.

20 Claims, No Drawings

OLEFIN POLYMERIZATION PROCESS

FIELD OF THE INVENTION

This invention relates to a process for polymerizing olefins over a fixed bed of solid acid catalyst. More specifically, the invention is an improved method for practicing such a process which involves reactivation of the catalyst while the catalyst is simultaneously used as an olefin conversion catalyst.

BACKGROUND OF THE INVENTION

A variety of commercial chemical and petrochemical processes involve the condensation reaction of an olefin or a mixture of olefins over an acid catalyst to form higher molecular weight products. This type of condensation reaction is referred to herein as a polymerization process, and the products can be either low molecular weight oligomers or high molecular weight polymers. Oligomers are formed by the condensation of 2, 3 or 4 olefin molecules with each other, while polymers are formed by the condensation of 5 or more olefin molecules with each other. As used herein, the term "polymerization" is used to refer to a process for the formation of oligomers and/or polymers.

Low molecular weight olefins (such as propene, 2-methylpropene, 1-butene and 2-butene) can be converted by polymerization over a solid acid catalyst (such as a solid phosphoric acid catalyst) to a product which is comprised of oligomers and is of value as a high-octane gasoline blending stock and as a starting material for the production of chemical intermediates and end-products which include alcohols, detergents and plastics. Such a process is typically carried out over a fixed bed of solid acid catalyst at elevated temperatures and pressures in either a chamber reactor or a tubular reactor. A plurality of reactors is ordinarily used in the practice of such a process so that individual reactors can be taken out of service for catalyst replacement or other maintenance without shutting down the other reactors of the process unit. In addition, reaction conditions in the process unit may be optimized through the use of two or more reactors in series.

The acid catalyzed alkylation of aromatic compounds with olefins is a well-known reaction which is of commercial importance. For example, ethylbenzene, cumene and detergent alkylate are produced by the alkylation of benzene with ethylene, propylene and $C_{10}$ to $C_8$ olefins, respectively. Sulfuric acid, HF, phosphoric acid, aluminum chloride, and boron fluoride are conventional catalysts for this reaction. In addition, solid acids which have comparable acid strength can also be utilized to catalyze this process, and such materials include amorphous and crystalline aluminosilicates, clays, ion-exchange resins, mixed oxides and supported acids such as solid phosphoric acid catalysts.

When a fixed bed of solid acid catalyst is used to catalyze the polymerization of olefins, the catalyst typically undergoes a slow deactivation. In addition, catalyst deactivation is sometimes accompanied by an increased pressure drop through the catalyst bed. Deactivation is observed as a loss of catalyst activity with the passage of time, and it typically results from the formation of by-products which accumulate on the surface of the catalyst and in catalyst pores. These by-products have the effect of encapsulating the catalyst, thereby hindering or preventing fresh reactants in the feedstock from contacting the catalyst. Any increase in the pressure drop across the catalyst bed, which accompanies catalyst deactivation, is typically a result of the deposit of by-products in the void space between catalyst particles. After a certain level of catalyst deactivation and/or increase in pressure drop across the catalyst bed takes place, economic considerations generally require either that the catalyst be regenerated or that it be replaced with fresh catalyst.

The choice between replacement and regeneration of deactivated catalyst depends on a number of factors which include the cost of fresh catalyst, the disposal cost of deactivated catalyst if it is to be discarded, and the cost and effectiveness of catalyst regeneration procedures. A particularly important consideration is the amount of time that the polymerization unit must be taken out of service in order to replace or regenerate deactivated catalyst. The shutdown of a polymerization unit for such a purpose ordinarily carries a significant economic penalty and, accordingly, any shutdown period must be minimized.

In the case of an olefin polymerization unit which is operated with a solid phosphoric acid catalyst, deactivated catalyst is ordinarily discarded and replaced with fresh catalyst. The solid phosphoric acid catalyst is relatively inexpensive, and satisfactory regeneration options are typically not available for this type of catalyst. Accordingly, economic considerations generally dictate a replacement of the catalyst rather than regeneration.

U.S. Pat. No 4,028,430 (Stine et al.) is directed to a continuous catalytic reaction process utilizing a simulated moving catalyst bed to effect, simultaneously, a catalyzed reaction in one zone and catalyst reactivation in another zone of a catalyst bed which contains at least three zones. The zones are arranged in series with a fluid flow path connecting each adjacent zone and also connecting the first and last zones in the series. By periodic alteration of the composition of the fluids that are passed into each zone, the site of the catalyzed reaction and the location of catalyst reactivation can be periodically moved from one zone to the next in the series to provide a simulated moving catalyst bed process. It is disclosed that the process can be applied to catalyzed reactions such as alkylation, diolefin saturation, hydrocracking, catalytic cracking, desulfurization, dehydrogenation, polymerization, isomerization, reforming, and flue gas desulfurization. It is further disclosed that one suitable type of reactivation involves flushing tars, polymers, high molecular weight hydrocarbons, residue, or particulate matter out of a catalyst with a suitable dissolving or flushing agent.

Canadian Patent No. 1,055,921 (Burton et al.) discloses that a bed of solid phosphoric acid catalyst which has been deactivated by the deposition on the catalyst particles of polymerized and carbonized hydrocarbonaceous materials can be reactivated in situ by: (a) inundating the deactivated catalyst at a temperature of 40° to 370° C. and a pressure of 1 and ⅓ to 100 atmospheres, absolute, in a reactivating liquid mixture of hydrocarbons which is substantially free from sulfur, which contains at least 5 weight percent aromatics and which boils within the range of 40° to 230° C.; (b) withdrawing the reactivating liquid from the catalyst; and (c) repeating steps (a) and (b) above at least one time. It is further disclosed that a catalytic reformate can be used as the reactivating liquid, and that the deactivated catalyst can be from a polymerization unit which is used for the production of motor fuel from light olefinic gases. U.S. Pat. No. 4,062,801 (Burton et al.) discloses a similar process which involves regenerating a bed of deactivated catalyst through the use of a cycle of the following steps, wherein the cycle is carried out three times: (1) immersing the catalyst bed in a hot, aromatic hydrocarbon-containing liquid by passing the liquid upward into the catalyst bed; (2) soaking the catalyst bed in the liquid for at least 30 minutes at a temperature above about 280° F.; and (3) draining the liquid from the catalyst.

U.S. Pat. No. 5,648,579 (Kulprathipanja et al.) is directed to a continuous process for conducting a catalyzed reaction in a single fixed bed of catalyst wherein catalyst deactivation is prevented through the use of periodic regeneration cycles, and wherein a regeneration cycle involves washing deactivating materials from the catalyst with a desorbent. The catalyzed reaction itself is terminated during each regeneration cycle by terminating the flow of one or more of the reactants. When applied to the alkylation of aromatics with olefins, the process is characterized by: (1) a reaction cycle, when both olefin and aromatic flow into the catalyst zone to effect alkylation, and (2) a flush cycle when only a desorbent flows into the catalyst zone. It is disclosed that this type of process can be applied to the alkylation of aromatics with alkylating agents, the alkylation of $C_3$–$C_6$ olefins with alkanes in the $C_4$–$C_6$ range, olefin hydration, ether formation by reaction of olefins with alcohols, and ester formation by reaction of organic acids with alcohols.

SUMMARY OF THE INVENTION

Olefin polymerization which is carried out over a fixed bed of catalyst is typically accompanied by catalyst deactivation which is observed as a loss of catalyst activity with the passage of time. In addition, catalyst deactivation is sometimes accompanied by an increased pressure drop through the fixed bed of catalyst. Any such deactivation or increased pressure drop will have an adverse effect on the process, and at some point will require that the deactivated catalyst either be regenerated or replaced. Unfortunately, each of these alternatives has an associated economic penalty. Regeneration of the catalyst requires that the deactivated catalyst bed be taken out of service during the regeneration process, and this typically requires that a second "swing" catalyst bed be available for use during the regeneration process in order to avoid the waste of olefinic feedstock or the disruption of associated processes that produce the olefinic feedstock. Replacement of deactivated catalyst will also require that the catalyst bed be taken out of service during the replacement process, and this will also typically require that a second "swing" catalyst bed be available for use during this replacement period for the same reasons. In addition, catalyst replacement results in additional penalties which include the cost of replacement catalyst and the cost of disposing of deactivated catalyst. In view of these penalties, catalyst regeneration or replacement is frequently delayed longer than might otherwise be desirable for efficient process operation.

We have discovered a method for regenerating a fixed bed of olefin polymerization catalyst which can be performed without taking the catalyst bed out of service. Accordingly, we have discovered a method which avoids the cost of a standby "swing" reactor. In addition, we have discovered a catalyst regeneration method which does not impose any significant penalty in terms of either cost or process disruption. Therefore, our process can be used to maintain high catalyst activity and efficient operation of an olefin polymerization unit.

One embodiment of the invention is a process for the polymerization of olefins using a fixed bed of solid acid catalyst which comprises:

(a) contacting a first olefin-containing feedstock with the fixed bed of solid acid catalyst under olefin polymerization conditions by passing the first feedstock into the fixed bed and withdrawing a product stream from the fixed bed, wherein the mole ratio of olefins to aromatic compounds in said first feedstock is at least about 12, and whereby the acid catalyst undergoes deactivation with the passage of time;

(b) substituting a second olefin-containing feedstock for the first feedstock after the acid catalyst has become partially deactivated, wherein the second feedstock contains aromatic compounds and the mole ratio of olefins to aromatic compounds in said second feedstock is in the range from about 1 to about 10;

(c) contacting the second feedstock with the fixed bed of solid acid catalyst under olefin polymerization conditions by passing the second feedstock into the fixed bed and withdrawing a product stream from the fixed bed; and (d) passing the second feedstock into the fixed bed and withdrawing said product stream from the fixed bed for a period of time which is effective to produce a regenerated acid catalyst which has an increased activity relative to that at the beginning of step (b).

Another embodiment of the invention is a continuous process for the catalyzed polymerization of olefins using a fixed bed of solid acid catalyst which comprises alternating a first polymerization cycle with a second polymerization cycle wherein:

(a) the first polymerization cycle is comprised of:
  (i) passing a first olefin-containing feedstock into the catalyst bed, wherein the mole ratio of olefins to aromatic compounds in said first feedstock is at least about 12;
  (ii) polymerizing at least a portion of the olefin content of the first feedstock under olefin polymerization conditions in the catalyst bed, whereby the catalyst undergoes deactivation with the passage of time; and
  (iii) withdrawing a product stream from the catalyst bed which is comprised of olefin polymers; and (b) the second polymerization cycle is comprised of:
  (i) substituting a second olefin-containing feedstock for the first feedstock, wherein the second feedstock contains aromatic compounds and the mole ratio of olefins to aromatic compounds in said second feedstock is in the range from about 1 to about 10;
  (ii) converting at least a portion of the olefin content of the second feedstock to reaction products under olefin polymerization conditions in the catalyst bed, wherein said products are comprised of olefin polymers and alkylated aromatic compounds;
  (iii) withdrawing a product stream from the catalyst bed; and
  (iv) continuing the second polymerization cycle for a period of time which is effective to produce a regenerated acid catalyst which has an increased activity relative to that at the beginning of the second polymerization cycle.

An object of the invention is to provide an improved process for the polymerization of olefins over a fixed bed of solid acid catalyst.

An object of the invention is to provide a method for the regeneration of a fixed bed of olefin polymerization catalyst which can be carried out while the catalyst is simultaneously used to catalyze the polymerization of olefins.

An object of the invention is to provide a process for the polymerization of olefins over a fixed bed of solid acid catalyst in a reactor wherein high catalyst activity can be maintained over long periods of time without any need to shut the reactor down for catalyst regeneration or replacement.

A further object of the invention is to provide a method for the periodic regeneration of a fixed bed of olefin polymerization catalyst which does not significantly interfere with the normal use of the fixed bed to catalyze olefin polymerization.

Another object of the invention is to provide an improved method for maintaining high catalyst activity in a process wherein a fixed bed of solid phosphoric acid catalyst is utilized to catalyze the conversion of low molecular weight olefins to oligomers.

DETAILED DESCRIPTION OF THE INVENTION

The present invention relates to a process for polymerizing olefins over a fixed bed of solid acid catalyst and is directed to a method which can be used to regenerate or maintain the activity of the catalyst without terminating the use of the fixed bed to catalyze olefin polymerization. The method involves the use of two different olefin-containing feedstocks which are referred to herein either as the first and second olefin-containing feedstocks or as the first and second feedstocks, respectively. The first feedstock is a conventional olefin-containing feedstock which contains little if any content of aromatic compounds, and causes the catalyst to undergo slow deactivation as a result of the formation of by-products which accumulate on the surface of the catalyst and in catalyst pores. In contrast, the second feedstock contains a significant concentration of aromatic compounds and has the ability to regenerate the deactivated catalyst. In the practice of the invention, the second feedstock is substituted for the first feedstock whenever catalyst regeneration is deemed appropriate, and the flow of the second feedstock to the catalyst bed is continued for a period of time which is effective to at least partially regenerate the catalyst. In a preferred embodiment, the second feedstock is periodically substituted for the first feedstock in order to maintain high catalyst activity.

The olefin conversion process of this invention can be carried out with cyclic olefins, substituted cyclic olefins, and olefins of formula I wherein $R_1$ is a hydrocarbyl group and each $R_2$ is independently selected from the group consisting of hydrogen and hydrocarbyl groups. Preferably, $R_1$ is an alkyl group and each $R_2$ is independently selected from the group consisting of hydrogen and alkyl groups.

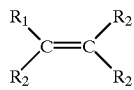

(I)

Examples of suitable cyclic olefins and substituted cyclic olefins include cyclopentene, 1-methylcyclopentene and cyclohexene. Examples of suitable olefins of the type of formula I include propene, 2-methylpropene, 1-butene, 2-butene, 2-methyl-1-butene, 3-methyl-1-butene, 2-methyl-2-butene, 2,3-dimethyl-1-butene, 3,3-dimethyl-1-butene, 2,3-dimethyl-2-butene, 2-ethyl-1-butene, 1-pentene, 2-pentene, 2-methyl-1-pentene, 3-methyl-1-pentene, 4-methyl-1-pentene, 1-hexene, 2-hexene, and 3-hexene.

Preferred olefins for use in the practice of the olefin conversion process of this invention will contain from 3 to 6 carbon atoms, and highly preferred olefins will contain 3 or 4 carbon atoms. If desired, the first and second olefin-containing feedstocks for the olefin conversion process of this invention can comprise a mixture of different olefins. Alternatively, either or both the first and second feedstocks can be comprised of a single olefin. It will be appreciated that the first and second feedstocks can comprise materials other than olefins, such as diluents which are substantially inert under the reaction conditions utilized in the polymerization process. For example, either or both the first and second feedstocks can contain substantial quantities of saturated hydrocarbons, such as normal paraffins, which will be relatively unreactive under the conditions of the olefin conversion process of this invention. Indeed, a normal paraffin such as propane or butane can be used as a diluent and as a recycle material for use in managing the heat which is produced by the exothermic olefin conversion reactions.

The first olefin-containing feedstock is a conventional feedstock for an olefin polymerization process which contains little if any content of aromatic compounds. In one embodiment of the invention, the first olefin-containing feedstock will be substantially free of aromatic compounds. However, if desired, the first olefin-containing feedstock can comprise a minor amount of one or more aromatic compounds. When aromatic components are present, alkylation of these components by the olefin or olefins of the first olefin-containing feedstock can be carried out simultaneously with olefin polymerization. Desirably, the mole ratio of olefins to aromatic compounds in the first olefin-containing feedstock will be at least about 12, preferably at least about 15, and more preferably at least about 18. In such an embodiment, volatile low molecular weight aromatic compounds such as benzene, which are undesirable as gasoline components because of toxicity considerations, can be converted to less volatile materials, which are highly desirable gasoline components, by alkylation. For example, benzene and toluene can be converted to cumene and cymene, respectively, by monoalkylation with propene. Such a blending of olefin polymerization and alkylation of aromatics is a particularly desirable process for use in the manufacture of gasoline blending stock. In such an embodiment, low molecular weight olefins which contain from 3 to 4 carbon atoms can be used to alkylate benzene, and excess olefins are converted to oligomers. All of these products are of high octane and are desirable gasoline components.

Aromatic compounds which can be included in the first olefin-containing feedstock include all organic compounds of from 6 to 20 carbon atoms which contain aromatic functionality and can be alkylated by an olefin in the presence of an acid catalyst. Such materials include both aromatic compounds and substituted aromatic compounds which carry one or more substituents. Aromatic hydrocarbons and hydrocarbyl-substituted aromatic hydrocarbons which contain from 6 to 10 carbon atoms are particularly suitable. In addition, mixtures of such materials can be used as a component of the first olefin-containing feedstock in the practice of this invention. Examples of such materials include compounds of formula II which contain from 6 to 20 carbon atoms where each R is independently selected from the group consisting of hydrogen and hydrocarbyl groups. However, preferred aromatic compounds are hydrocarbons which contain from 6 to 10 carbon atoms and are of formula II where each R is independently selected from the group consisting of hydrogen and alkyl of

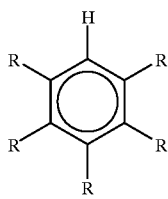

(II)

from 1 to 3 carbon atoms. Benzene and toluene are particularly preferred.

Aromatic compounds for inclusion in the first olefin-containing feedstock to the olefin polymerization process of this invention can be obtained from any desired source. However, when gasoline blending stocks are manufactured in a petroleum refinery through the use of the olefin polymerization process, catalytic cracking units, reformers and isomerization units are convenient sources of the aromatic components. For example, a light reformate can be used, and a typical material of this type will have a total aromatic content of about 35 vol. % and will contain about 10 vol. % of benzene. If the first olefin-containing feedstock is prepared by combining about 10 vol. % of such a light reformate with about 90 vol. % of a $C_3$ to $C_4$ feedstock which contains about 45 vol. % of propylene and butylenes which are mixed with propane and butanes, about 80% of the benzene in this feedstock can be alkylated in a conventional olefin polymerization unit which uses a solid phosphoric acid catalyst.

In the practice of this invention, a typical first olefin-containing feedstock to a polymerization unit for conversion to oligomers in the gasoline boiling range will comprise a mixture of propane, butane, 1-methylpropane, propene, 1-butene, 2-butene and 1-methylpropene, wherein the olefin concentration is in the range from about 35 vol. % to about 60 vol. %. However, it will be appreciated that the first olefin-containing feedstock can have a variety of other compositions which include, but are not limited to, other olefins or olefin mixtures, other diluents, and the presence of a minor amount of aromatic compounds. In addition, olefin concentrations can be used which are outside this range.

The second olefin-containing feedstock which is used in the practice of this invention differs from the first olefin-containing feedstock in that it contains a significant concentration of aromatic compounds which will be greater than any minor concentration of aromatics in the first feedstock. Desirably, the mole ratio of olefins to aromatic compounds in the second olefin-containing feedstock will be in the range from about 1 to about 10, preferably from about 2 to about 8, and more preferably from about 3 to about 8.

Aromatic compounds which can be included in the second olefin-containing feedstock are the same as those which are suitable for use in the first olefin-containing feedstock. As stated above, these aromatic compounds include all organic compounds of from 6 to 20 carbon atoms which contain aromatic functionality and can be alkylated by an olefin in the presence of an acid catalyst. Such materials include both aromatic compounds and substituted aromatic compounds which carry one or more substituents. Aromatic hydrocarbons and hydrocarbyl-substituted aromatic hydrocarbons which contain from 6 to 10 carbon atoms are particularly suitable. Preferred aromatic compounds for use as components of the second olefin-containing feedstock are of formula II where each R is independently selected from the group consisting of hydrogen and alkyl of from 1 to 3 carbon atoms. In addition, preferred aromatic compounds are liquids which have a boiling point in the range from about 20° to about 250° C. at atmospheric pressure. Benzene and toluene are particularly preferred.

Aromatic compounds for inclusion in the second olefin-containing feedstock to the olefin polymerization process of this invention can be obtained from any desired source. However, as disclosed above, when gasoline blending stocks are manufactured in a petroleum refinery through the use of the olefin polymerization process, catalytic cracking units, reformers and isomerization units are convenient sources of the aromatic components. A light reformate is a highly desirable source of suitable aromatic compounds, and a typical material of this type will have a total aromatic content of about 35 vol. % and will contain about 10 vol. % of benzene.

In one embodiment of the invention, the second olefin-containing feedstock is comprised of from about 20 to about 80 vol. % of a substantially olefin-free hydrocarbon fluid which boils within the range from about 20° to about 250° C. at atmospheric pressure and contains at least about 5 vol. % of aromatics (this hydrocarbon fluid is referred to herein as the "substantially olefin-free hydrocarbon fluid"). For example, the second feedstock can be prepared by replacing from about 20 to about 80 vol. % of the first feedstock with the substantially olefin-free hydrocarbon fluid. Although the substantially olefin-free hydrocarbon fluid will desirably boil within the range from about 20° to about 250° C., a preferred range is from about 20° to about 180° C., and a highly preferred range is from about 30° to about 130° C. In addition, this fluid will contain desirably at least about 5 vol. % of aromatics, preferably at least about 20 vol. % of aromatics, and more preferably at least about 30 vol. % of aromatics. Typically, this fluid will contain from about 15 to about 85 vol. % aromatics. Finally, the substantially olefin-free hydrocarbon fluid will have an olefin content which is desirably less than 5 vol. %, preferably less than 3 vol. %, and more preferably less than 2 vol. %.

In a petroleum refinery, naphthas, reformates and blends of aromatic and aliphatic hydrocarbons can be used as the substantially olefin-free hydrocarbon fluid. However, a reformate is preferred. A typical light reformate which is highly suitable for use in the practice of this invention will contain from about 0 to about 2 vol. % olefins, from about 20 to about 45 vol. % aromatics, and will have distillation properties such that the 10% distillation point ("T10") is no greater than about 160° F. (71° C.), the 50% distillation point ("T50") is no greater than about 200° F. (93° C.), and the 90% distillation point ("T90") is no greater than about 250° F. (121° C.). It will be understood that these distillation points refer to a distillation point obtained by the ASTM D 86-95 procedure (which can be found in the 1996 Annual Book of ASTM Standards, Section 5, Petroleum Products, Lubricants, and Fossil Fuels) or by conventional alternative procedures. A typical light reformate will contain from about 5 to about 15 vol. % of benzene.

The aromatics of the substantially olefin-free hydrocarbon fluid are of critical importance and will be of the type defined above as being suitable for use as components of the second olefin-containing feedstock.

When the second olefin-containing feedstock of this invention is prepared by substituting the substantially olefin-free hydrocarbon fluid for a portion of the first olefin-containing feedstock, said fluid will be used in an amount which is effective to provide a mole ratio of olefins to aromatics in the resulting mixture which is in the range from about 1 to about 10.

Any solid acidic material which can catalyze the polymerization of an olefin can be used as a catalyst in the practice of this invention, and such materials include liquid acids which are supported on a solid substrate. Desirably, the solid acidic catalyst will also have the ability to catalyze the alkylation of aromatic compounds by olefins. As a practical matter, most solid acidic materials which are able to catalyze olefin polymerization possess this ability. In the practice of the olefin polymerization process of this invention, the olefin-containing feedstock can simply be passed through a particulate fixed bed of a solid acidic catalyst at a suitable temperature and pressure.

Catalysts which are suitable for use in the practice of this invention can be comprised of materials such as acidic polymeric resins, supported acids, and acidic inorganic oxides. Suitable acidic polymeric resins include the polymeric sulfonic acid resins, which are well known in the art and are commercially available. Amberlyst® 35, a product of Rohm and Haas Co., is a typical example of such a material.

Supported acids which are useful as catalysts include, but are not limited to, Brönsted acids (examples include phosphoric acid, sulfuric acid, boric acid, HF, fluorosulfonic acid, trifluoromethanesulfonic acid, and dihydroxyfluoroboric acid) and Lewis acids (examples include $BF_3$, $BCl_3$, $AlCl_3$, $AlBr_3$, $FeCl_2$, $FeCl_3$, $ZnCl_2$, $SbF_5$, $SbCl_5$ and combinations of $AlCl_3$ and HCl) which are supported on solids such as silica, alumina, silica-aluminas, zirconium oxide or clays. When liquid acids are employed, the supported catalysts are typically prepared by combining the desired liquid acid with the desired support and then drying.

Acidic inorganic oxides which are useful as catalysts include, but are not limited to, aluminas, silica-aluminas, natural and synthetic pillared clays, and natural and synthetic zeolites such as faujasites, mordenites, L, omega, X, Y, beta, and ZSM. Highly suitable zeolites include beta, Y, ZSM-3, ZSM-4, ZSM-5, ZSM-18, and ZSM-20. If desired, the zeolites can be incorporated into an inorganic oxide matrix material such as a silica-alumina.

Catalysts can comprise mixtures of different materials, such as a Lewis acid (examples include $BF_3$, $BCl_3$, and $AlCl_3$), a nonzeolitic solid inorganic oxide (such as silica, alumina and silica-alumina), and a large-pore crystalline molecular sieve (examples include zeolites, pillared clays and aluminophosphates).

Supported catalysts which are prepared by combining a phosphoric acid with a support are often used in olefin polymerization processes and are highly preferred for use in the practice of this invention. Such catalysts are referred to herein as solid phosphoric acid catalysts.

A solid phosphoric acid catalyst is normally prepared by mixing a phosphoric acid, such as ortho-phosphoric acid, pyro-phosphoric acid or tetra-phosphoric acid, with a siliceous solid carrier to form a wet paste. This paste may be calcined and then crushed to yield catalyst particles, or the paste may be extruded or pelleted prior to calcining to produce more uniform catalyst particles. The carrier is typically a naturally occurring, porous silica-containing material such as kieselguhr, kaolin, infusorial earth or diatomaceous earth. A minor amount of various additives, such as mineral talc, fullers earth and iron compounds, including iron oxide, can be added to the carrier to increase its strength and hardness. The combination of the carrier and the additives normally comprises about 15–30 wt. % of the catalyst, with the remainder being the phosphoric acid. However, the amount of phosphoric acid used in the manufacture of the catalyst can vary from about 8 to 80 wt. % of the catalyst. Solid phosphoric acid catalysts are available commercially, and such a material is available from UOP under the name SPA-2. This SPA-2 catalyst is a cylindrical extrudate having the following properties: (1) a nominal diameter of 4.75 mm; (2) a loaded density of 0.93 g/cm$^3$; (3) a free phosphoric acid content, calculated as $P_2O_5$, of 16 to 20 wt. %; and (4) a nominal total phosphoric acid content, calculated as $P_2O_5$, of 60 wt. %. The preparation and properties of conventional solid phosphoric acid catalysts are set forth in U.S. Pat. No. 2,120,702 (Ipatieff et al.); U.S. Pat. No. 3,050,472 (Morrell); U.S. Pat. No. 3,050,473 (Morrell) and U.S. Pat. No. 3,132,109 (Morrell); and also in British Patent No. 863,539. These patents are incorporated herein by reference.

The olefin polymerization process of this invention is carried out in a fixed bed of the solid acid catalyst. If desired, the catalyst can be located in a chamber reactor or a tubular reactor. In a tubular reactor, the catalyst is contained in a multiplicity of small tubes which are surrounded with a circulating cooling medium. These tubes will typically have an internal diameter of from about 5 cm to about 15 cm, although other diameters can also be used. A tubular reactor is frequently preferable to a chamber reactor because it permits a closer control of the reaction temperature and can be easily constructed for high pressure operation. Ordinarily, a plurality of reactors will be used. For example, an olefin polymerization unit employing tubular reactors can have as many as eight or more reactors. The heat produced by the exothermic olefin conversion reactions can be controlled in a chamber reactor by using a saturated hydrocarbon as a recycle from reactor effluent to reactor feedstock and/or as a quench between multiple catalyst beds within the reactor. The temperature in tubular reactors is typically controlled by water or oil circulation around the reactor tubes.

In the practice of the olefin polymerization process of this invention, the first olefin-containing feedstock is contacted with the solid acid catalyst at a temperature, pressure and period of time which are effective to result in conversion of at least a portion of the olefins in the first feedstock to the desired products, such as oligomers which are useful as a gasoline blending stock or as a petrochemical feedstock. Desirably, the contacting temperature will be in excess of about 50° C., preferably in excess of 100° C., and more preferably in excess of 125° C. The contacting will generally be carried out at a temperature in the range from about 50° to about 350° C., preferably from about 100° to about 350° C., and more preferably from about 125° to about 250° C. It will be appreciated, of course, that the optimum temperature will be a function of the specific solid acid catalyst used and the specific olefins and their concentration in the first feedstock. However, for typical solid phosphoric acid catalysts used in combination with propylene and/or butylenes, the reaction temperature will usually be in the range from about 150° to about 250° C.

In the practice of the olefin polymerization process of this invention, the first olefin-containing feedstock can be contacted with the solid acid catalyst at any suitable pressure. However, pressures in the range from about 0.01 to about 200 atmospheres are desirable, and a pressure in the range from about 1 to about 100 atmospheres is preferred. When a typical solid phosphoric acid catalyst is used for the conversion of propylenes and/or butylenes to gasoline blending stock, the pressure will usually be in the range from about 20 to about 90 atmospheres.

In the practice of this process, the first olefin-containing feedstock is contacted with the fixed bed of solid acid catalyst under olefin polymerization conditions by passing the first feedstock into the fixed bed and withdrawing a product stream from the fixed bed which is comprised of olefin polymers. As a consequence of this contacting, the acid catalyst undergoes deactivation with the passage of time.

The above-described conditions of temperature and pressure, which are suitable for use in the practice of this invention for the conversion of at least a portion of the olefins in the first olefin-containing feedstock to olefin polymers, are referred to herein as "olefin polymerization conditions." These same olefin polymerization conditions are also used when the second olefin-containing feedstock of this invention is contacted with the fixed bed of catalyst. More specifically, the feedstock is contacted with the fixed bed of solid acid catalyst under olefin polymerization conditions by passing the second feedstock into the fixed bed and withdrawing a product stream from the fixed bed. This contacting with the second feedstock is continued for a period of time which is effective to produce a regenerated acid catalyst which has an increased activity relative to that at the beginning of the contacting with said second feedstock.

In one embodiment of the invention, a substantially constant flow of feedstock is maintained through the fixed bed of solid acid catalyst when one feedstock is replaced by the other (i.e., substantially the same flow rate is used for both feedstocks). In another embodiment of the invention, a substantially constant temperature and pressure is maintained in the fixed bed of solid acid catalyst when one feedstock is replaced by the other (i.e., substantially the same temperature and pressure are used for both feedstocks).

Most solid acid catalysts which are suitable for catalyzing the polymerization of olefins are also excellent catalysts for promoting the alkylation of aromatic compounds by olefins under similar or identical reaction conditions. In view of the fact that the second olefin-containing feedstock contains aromatic compounds, alkylation of these aromatic compounds by the olefin or olefins in the feedstock will compete with olefin polymerization. As a result, both olefin polymers and alkylated aromatic compounds will be obtained as products, and the ratio of these products will be a function of the mole ratio of olefins to aromatic compounds in the second olefin-containing feedstock. For example, when the mole ratio of olefins to aromatic compounds is about 1, the formation of products from alkylation of the aromatic compounds may predominate over the formation of olefin polymerization products. However, when the mole ratio of olefins to aromatic compounds is about 10, the formation of olefin polymers will typically predominate.

As described above, volatile low molecular weight aromatic compounds such as benzene, which are undesirable as gasoline components because of toxicity considerations, can be converted to less volatile materials, which are highly desirable gasoline components, by alkylation. Such a combination of polymerization and alkylation is particularly desirable when the product is intended for use as a gasoline blending stock.

In a preferred embodiment of the invention, a continuous process is carried out wherein the first feedstock is the principal feedstock for the process, and the second feedstock is periodically substituted for the first feedstock whenever the fixed bed of catalyst requires regeneration.

Catalyst deactivation which occurs during olefin polymerization in a fixed bed of catalyst using a conventional olefin-containing feedstock is believed to be primarily a result of the formation of high boiling polymers as by-products. These by-products can then remain on the catalyst and undergo further conversion to even higher molecular weight polymers which resemble heavy tars and, in some cases, even have the appearance of a coke-like material. These materials can coat the catalyst particles and plug pores in the catalyst, thereby causing catalyst deactivation. It is also believed that impurities may occasionally occur in the olefin-containing feedstock which can cause deactivation. Such impurities include but are not limited to ethers such as dimethyl ether and methyl isopropyl ether. It is believed that such ethers can cause catalyst deactivation by adsorption onto the catalyst.

As a consequence of its relatively high aromatic content, the second feedstock of this invention is a better solvent than the first feedstock. Accordingly, it is believed that the second feedstock is more effective than the first feedstock in: (1) dissolving or eluting undesired polymers and tars from the catalyst; and (2) removing any other adsorbed catalyst poisons from the catalyst. This removal of deactivating materials from deactivated catalyst by the second feedstock is most effective when the two are contacted at elevated temperatures, such as those which are used for the polymerization of olefins in the first feedstock over the catalyst.

EXAMPLE

The conversion of $C_3$ and $C_4$ olefins to high octane gasoline blending stock by conversion to dimers and trimers was carried out over a solid phosphoric acid catalyst (SPA-2, sold by UOP) in a polymerization unit which contained eight tubular reactors (identified as Reactors A–H). However, one of the reactors (Reactor D) was out of service at the time of this experiment. The normal feedstock to the unit was prepared by blending a minor amount of light reformate (typically from about 10 to about 23 vol. %) with an olefin-containing $C_3$–$C_4$ stream. As a consequence of operation of the polymerization unit over a substantial period of time using the normal feedstock, the catalyst had undergone significant deactivation.

A regeneration feedstock was prepared by blending a much larger amount of light reformate with the olefin-containing $C_3$–$C_4$ stream, and this regeneration feedstock was substituted for the normal feedstock for a period of eight hours. At the end of the eight hour regeneration period, operation of the polymerization unit was resumed using the normal feedstock. Operating conditions for the polymerization unit with the normal feedstock, measured seven hours before beginning use of the regeneration feedstock and nine hours after terminating use of the regeneration feedstock, are set forth in Table I. The compositions of the olefin-containing $C_3$–$C_4$ 5 stream and the light reformate, seven hours before the regeneration period, during the regeneration period, and nine hours after the regeneration period, are set forth in Tables II and III, respectively. These compositions are typical for the olefin-containing $C_3$–$C_4$ stream and the light reformate which were used in the polymerization unit during the substantial period of time prior to the catalyst regeneration period and during which catalyst deactivation had occurred.

Over the eight hour regeneration period, the amount of light reformate charged to the polymerization unit varied from 900 to 3800 bpd (143,100 to 604,100 liters/day) and averaged 2765 bpd (439,600 liters/day). During the same regeneration period, the amount of the $C_3$–$C_4$ stream charged to the polymerization unit varied from 2519 to 6459 bpd (400,500 to 1,026,900 liters/day) and averaged 3699 bpd (588,100 liters/day). Accordingly, the regeneration feedstock, over the eight hour regeneration period, consisted of about 43 vol. % of light reformate and contained about 13.9 vol. % aromatics and about 22.7 vol. % $C_3$–$C_4$ olefins. The above indicated variation in flow rate of light reformate during the regeneration test period was a consequence of pumping and surge drum constraints.

During the regeneration period, the conversion of olefins in the regeneration feedstock provided sufficient heat of reaction to keep the reactor inlet temperatures essentially unchanged at 186° to 188° C. relative to the 186 to 196° C. observed during operation of the polymerization unit with normal feedstock shortly before and shortly after the regeneration period. Reactor outlet temperatures during the regeneration period were also substantially the same as those before and after the regeneration period. The inlet pressure during the regeneration period averaged 80.8 atmospheres gauge.

The activity of the catalyst in the reactors of the polymerization unit was measured: (1) seven hours before beginning use of the regeneration feedstock; and (2) nine hours after terminating use of the regeneration feedstock. These activity values are set forth in Table IV and were calculated from the apparent rate constant for conversion of $C_3$ and $C_4$ olefins in the reactor in question. The apparent rate constants are based on data resulting from analysis of the reactor feedstock and effluent by gas chromatography. The data in Table IV demonstrate that the regeneration procedure resulted in an increase of catalyst activity in 6 of the 7 reactors. The improvement in activity, on average, is substantial and ranges from 10.6% in reactor A to 70.0% in reactor E.

TABLE I

Process Conditions in Olefin Polymerization Unit Prior to Regeneration and After Regeneration.

| Parameter or Variable | Before Regeneration | After Regeneration |
|---|---|---|
| Reactors in Service | 7 (Reactors A, B, C, B, F, G and H) | 7 (Reactors A, B, C, B, F, G and H) |
| Feedstock Flow Rates, bpd (liters/day) | | |
| Total Feedstock to Unit | 4,039 (642,100) | 3,683 (585,500) |
| Reactor A | 671 (106,700) | 706 (112,200) |
| Reactor B | 491 (78,100) | 497 (79,000) |
| Reactor C | 572 (90,900) | 571 (90,800) |
| Reactor E | 665 (105,700) | 688 (109,400) |
| Reactor F | 667 (106,000) | 683 (108,600) |
| Reactor G | 394 (62,600) | 442 (70,300) |
| Reactor H | 579 (92,100) | 580 (92,200) |
| Feedstock Composition, vol. % | | |
| Olefin-containing $C_3$–$C_4$ Stream | 82 | 77 |
| Light Reformate Stream | 18 | 23 |
| Pressure, atmospheres gauge | | |
| Unit Inlet | 79.1 | 78.3 |
| Inlet Temperature, ° C. | | |
| Reactors A, B, C and D | 186 | 186 |
| Reactors E, F, G and H | 196 | 190 |

TABLE II

Analysis of Olefin-containing $C_3$–$C_4$ Stream.

| Component, Vol. % | Before Regeneration | During Regeneration | After Regeneration |
|---|---|---|---|
| Methane | 0.0 | 0.0 | 0.0 |
| Ethane | 0.2 | 0.2 | 1.0 |
| Ethylene | 0.0 | 0.0 | 0.0 |
| Propane | 15.9 | 15.9 | 22.9 |
| Propene | 29.6 | 29.6 | 41.6 |
| Butane | 6.6 | 6.6 | 4.0 |
| 2-Methylpropane | 20.4 | 20.4 | 14.3 |
| $C_4$-Olefins | 22.5 | 22.5 | 11.8 |
| Pentane | 0.9 | 0.9 | 1.7 |
| 2-Methylbutane | 2.5 | 2.5 | 2.7 |

TABLE III

Analysis of Light Reformate Stream.

| Component, Vol. % | Before Regeneration | During Regeneration | After Regeneration |
|---|---|---|---|
| Olefins | 1.7 | 1.5 | 1.5 |
| Aromatics | 32.9 | 32.3 | 32.3 |
| Saturated Hydrocarbons | 65.3 | 66.3 | 66.3 |
| Benzene | 8.2 | 8.2 | 8.2 |

TABLE IV

Catalyst Activity Before and After Regeneration.

| Reactor | Catalyst Activity Before Shutdown | Catalyst Activity After Shutdown | Change in Catalyst Activity, % |
|---|---|---|---|
| A | 4.7 | 5.2 | +10.6 |
| B | 3.0 | 3.6 | +20.0 |
| C | 4.6 | 4.3 | −6.5 |
| E | 3.0 | 5.1 | +70.0% |
| F | 3.1 | 4.7 | +51.6% |
| G | 3.3 | 3.6 | +9.1 |
| H | 3.0 | 4.5 | +50.0 |

We claim:

1. A process for the polymerization of olefins using a fixed bed of solid acid catalyst which comprises:
    (a) contacting a first olefin-containing feedstock with the fixed bed of solid acid catalyst under olefin polymerization conditions by passing the first feedstock into the fixed bed and withdrawing a product stream from the fixed bed, wherein the mole ratio of olefins to aromatic compounds in said first feedstock is at least about 12, and whereby the acid catalyst undergoes deactivation with the passage of time;
    (b) substituting a second olefin-containing feedstock for the first feedstock after the acid catalyst has become partially deactivated, wherein the second feedstock contains aromatic compounds and the mole ratio of olefins to aromatic compounds in said second feedstock is in the range from about 1 to about 10;
    (c) contacting the second feedstock with the fixed bed of solid acid catalyst under olefin polymerization conditions by passing the second feedstock into the fixed bed and withdrawing a product stream from the fixed bed; and
    (d) passing the second feedstock into the fixed bed and withdrawing said product stream from the fixed bed for a period of time which is effective to produce a regenerated acid catalyst which has an increased activity relative to that at the beginning of step (b).

2. The process of claim 1 wherein the mole ratio of olefins to aromatic hydrocarbons in the first feedstock is at least about 15.

3. The process of claim 1 wherein the mole ratio of olefins to aromatic hydrocarbons in the second feedstock is in the range from about 3 to about 8.

4. The process of claim 1 wherein said process is continuous and steps (a) through (d) are periodically repeated.

5. A continuous process for the catalyzed polymerization of olefins using a fixed bed of solid acid catalyst which comprises alternating a first polymerization cycle with a second polymerization cycle wherein:
    (a) the first polymerization cycle is comprised of:
        (i) passing a first olefin-containing feedstock into the catalyst bed, wherein the mole ratio of olefins to aromatic compounds in said first feedstock is at least about 12;

(ii) polymerizing at least a portion of the olefin content of the first feedstock under olefin polymerization conditions in the catalyst bed, whereby the catalyst undergoes deactivation with the passage of time; and (iii) withdrawing a product stream from the catalyst bed which is comprised of olefin polymers; and (b) the second polymerization cycle is comprised of:

(i) substituting a second olefin-containing feedstock for the first feedstock, wherein the second feedstock contains aromatic compounds and the mole ratio of olefins to aromatic compounds in said second feedstock is in the range from about 1 to about 10;

(ii) converting at least a portion of the olefin content of the second feedstock to reaction products under olefin polymerization conditions in the catalyst bed, wherein said products are comprised of olefin polymers and alkylated aromatic compounds;

(iii) withdrawing a product stream from the catalyst bed; and (iv) continuing the second polymerization cycle for a period of time which is effective to produce a regenerated acid catalyst which has an increased activity relative to that at the beginning of the second polymerization cycle.

6. The process of claim 5 wherein the first feedstock is comprised of at least one olefin which is selected from the group consisting of olefins which contain from 3 to 6 carbon atoms.

7. The process of claim 6 wherein the first feedstock is comprised of at least one olefin which is selected from the group consisting of olefins which contain from 3 to 4 carbon atoms.

8. The process of claim 5 wherein the first feedstock comprises aromatic hydrocarbons and said aromatic hydrocarbons contain from 6 to 10 carbon atoms.

9. The process of claim 5 wherein the mole ratio of olefins to aromatic compounds in said first feedstock is at least about 15.

10. The process of claim 5 wherein the first feedstock is substantially free of aromatic compounds.

11. The process of claim 5 wherein the mole ratio of olefins to aromatic compounds in said second feedstock is in the range from about 3 to about 8.

12. The process of claim 5 wherein the aromatic compounds of said second feedstock contain from 6 to 10 carbon atoms.

13. The process of claim 5 wherein the second feedstock is comprised of from about 20 to about 80 vol. % of a substantially olefin-free hydrocarbon fluid which boils within the range from about 20° to about 250° C. at atmospheric pressure and contains at least about 5 vol. % aromatics.

14. The process of claim 13 wherein the substantially olefin-free hydrocarbon fluid is selected from the group consisting of naphthas, reformates and blends of aromatic and aliphatic hydrocarbons.

15. The process of claim 13 wherein the substantially olefin-free hydrocarbon fluid contains at least about 20 vol. % aromatics.

16. The process of claim 13 wherein the substantially olefin-free hydrocarbon fluid is a reformate.

17. The process of claim 5 wherein the solid acid catalyst is a solid phosphoric acid catalyst.

18. The process of claim 5 wherein a substantially constant flow of fluid is maintained through the fixed bed during both the first and second polymerization cycles.

19. The process of claim 5 wherein a substantially constant temperature and pressure is maintained in the fixed bed during both the first and second polymerization cycles.

20. The process of claim 5 wherein the product from said process comprises products boiling in the gasoline range.

* * * * *

UNITED STATES PATENT AND TRADEMARK OFFICE
CERTIFICATE OF CORRECTION

PATENT NO.: 6,025,534

DATED: February 15, 2000

INVENTOR(S): Anthony M. Valente, David B. Johnson, George A. Huff, Jr., Robert L. Mehlberg It is certified that error appears in the above-identified patent and that said Letters Patent is hereby corrected as shown below:

| Col. | Line  |                                                                              |                                              |
|------|-------|------------------------------------------------------------------------------|----------------------------------------------|
| 13   | 29-31 | "Before<br>Regeneration<br><br>7(Reactors A,<br>B,C,B,F,G and H)              | After     "<br>Regeneration<br><br>7(Reactors A,<br>B,C,B,F,G and H) |
|      |       | should-read:<br>"Before<br>Regeneration<br><br>7(Reactors A,<br>B,C,E,F,G and H) | After     "<br>Regeneration<br><br>7(Reactors A,<br>B,C,E,F,G and H) |

Signed and Sealed this

Twentieth Day of February, 2001

Attest:

NICHOLAS P. GODICI

Attesting Officer

Acting Director of the United States Patent and Trademark Office